(12) United States Patent
Chen et al.

(10) Patent No.: US 10,704,937 B2
(45) Date of Patent: Jul. 7, 2020

(54) CRITICAL FLOW NOZZLE FLOWMETER FOR MEASURING RESPECTIVE FLOWRATES OF GAS PHASE AND LIQUID PHASE IN MULTIPHASE FLUID AND MEASURING METHOD THEREOF

(71) Applicant: WUXI SEA PIONEERS TECHNOLOGIES CO. LTD, Wuxi (CN)

(72) Inventors: Jige Chen, Wuxi (CN); Zhiyong Wu, Wuxi (CN); Bin Xu, Wuxi (CN)

(73) Assignee: WUXI SEA PIONEERS TECHNOLOGIES CO. LTD, Wuxi (CN)

(*) Notice: Subject to any disclaimer, the term of this patent is extended or adjusted under 35 U.S.C. 154(b) by 0 days.

(21) Appl. No.: 16/339,380

(22) PCT Filed: Oct. 27, 2016

(86) PCT No.: PCT/CN2016/103629
§ 371 (c)(1),
(2) Date: Apr. 4, 2019

(87) PCT Pub. No.: WO2018/064850
PCT Pub. Date: Apr. 12, 2018

(65) Prior Publication Data
US 2019/0339102 A1 Nov. 7, 2019

(30) Foreign Application Priority Data

Oct. 9, 2016 (CN) .......................... 2016 1 0882309

(51) Int. Cl.
*G01F 1/42* (2006.01)
*G01N 23/095* (2018.01)
(Continued)

(52) U.S. Cl.
CPC ................. *G01F 1/42* (2013.01); *G01F 1/74* (2013.01); *G01N 23/095* (2018.02); *G01N 33/28* (2013.01); *G01N 2223/1013* (2013.01)

(58) Field of Classification Search
CPC ......................................................... G01F 1/42
See application file for complete search history.

(56) References Cited

U.S. PATENT DOCUMENTS

| 4,813,270 A * | 3/1989 | Baillie ...................... G01F 1/74 374/33 |
| 5,031,465 A | 7/1991 | Redus |
| | (Continued) | |

FOREIGN PATENT DOCUMENTS

| CN | 1494672 A | 5/2004 |
| CN | 201145592 Y | 11/2008 |
| | (Continued) | |

*Primary Examiner* — Raymond L Nimox
(74) *Attorney, Agent, or Firm* — Bayramoglu Law Offices LLC

(57) ABSTRACT

A method for measuring respective flowrates of gas phase and liquid phase in a multiphase fluid using a critical flow nozzle flowmeter. The critical flow nozzle flowmeter includes a throttling nozzle having an inlet, an outlet and a throat, and the throat has a smallest flow area for flowing fluid; a gamma ray detector, including a gamma ray emitter and a gamma ray receiver, arranged in a way allowing the gamma ray emitted by the gamma ray emitter to pass through a cross-section at the inlet of the throttling nozzle in a diametrical direction to reach the gamma ray receiver; pressure sensors respectively configured for measuring the pressure $P_1$ at the inlet of the throttling zone and the pressure $P_2$ at the outlet of the throttling nozzle; and a temperature sensor configured for measuring the temperature $T_1$ at the inlet of the throttling nozzle.

1 Claim, 2 Drawing Sheets

(51) Int. Cl.
    *G01F 1/74*       (2006.01)
    *G01N 33/28*    (2006.01)

(56) References Cited

U.S. PATENT DOCUMENTS

| | | | |
|---|---|---|---|
| 5,092,159 A | 3/1992 | Chien | |
| 2006/0248963 A1* | 11/2006 | Gulich | G01F 1/42 73/861.63 |
| 2007/0095136 A1* | 5/2007 | Hewitt | G01F 15/00 73/200 |
| 2014/0299210 A1* | 10/2014 | Atherton | G01F 1/74 137/624.27 |
| 2016/0076925 A1* | 3/2016 | Chen | G01F 1/44 702/49 |
| 2019/0219432 A1* | 7/2019 | Chen | G01F 1/74 |

FOREIGN PATENT DOCUMENTS

| | | |
|---|---|---|
| CN | 102435245 A | 5/2012 |
| CN | 103292849 A | 9/2013 |
| CN | 103867184 A | 6/2014 |
| CN | 104515562 A | 4/2015 |
| CN | 104533388 A | 4/2015 |
| CN | 105890689 A | 8/2016 |
| CN | 206114018 U | 4/2017 |
| TW | 200819712 A | 5/2008 |

* cited by examiner

CRITICAL FLOW NOZZLE FLOWMETER FOR MEASURING RESPECTIVE FLOWRATES OF GAS PHASE AND LIQUID PHASE IN MULTIPHASE FLUID AND MEASURING METHOD THEREOF

CROSS REFERENCE TO THE RELATED APPLICATIONS

This application is the national phase entry of International Application No. PCT/CN2016/103629, filed on 27 Oct. 2016, which is based upon and claims priority to Chinese Patent Application No. 201610882309.7, filed on 9 Oct. 2016, the entire contents of which are incorporated herein by reference.

TECHNICAL FIELD

The technical field of the invention belongs to multiphase fluid metering. In particular, the invention relates to a critical flow nozzle flowmeter useful for measuring respective flowrates of gas phase and liquid phase in a multiphase fluid and to a measuring method.

BACKGROUND

In the oil and gas industry, the oil well product refers to a gas and liquid mixed fluid simultaneously comprising liquid crude oil, water and natural gas, and the liquid and gas mixed liquid is called as "multiphase fluid" in the art. Said gas phase includes, for example, oil field gas or any gases which are non-condensable at room temperature, for example, such as methane, ethane, propane, butane and the like, and said liquid phase includes an oil phase, e.g., crude oil and other liquid additives which are dissolved in crude oil during the exploration of crude oil, and a water phase, e.g., formation water, water which is injected into oil wells during the exploration, and other liquid additives which are dissolved in the water phase. In practice, the phase separation between the oil phase and the water phase may occur, and it is also possible that the oil phase and the water phase are mixed together or entirely emulsified. How to real-time and accurately measure the gas flowrate and liquid flowrate in the gas and liquid mixed liquid explored from oil wells and how to further measure the flowrates of the oil, gas and water phases are essential for production management and production optimization. When the mass fraction of gas phase in a multiphase fluid is higher than 80%, the multiphase fluid is customarily called as "wet gas". Materials that explored from submarine oil and gas fields and shale all are wet gases.

When the oil well is a high-pressure well, the wellhead pressure is in an order of magnitude of tens of MPa. In order to control throughput of oil wells and wellhead pressure, an oil nozzle, as a throttling device, is widely used in petroleum chemistry. In practice, the oil nozzle is not only used as a device for control throughput of oil wells, but also required by customers to have a metering function.

In the prior art, the method for measuring respective flowrates of gas phase and liquid phase in a multiphase fluid is to combine a Venturi flowmeter and gamma ray technology, and its principals are described as follows: a Venturi tube is utilized to measure the total volume flowrate of a wet gas, and a single-energy gamma-ray detector is used to measure the respective phase fractions of the gas and liquid phases therein; then, the total volume flowrate multiplies by the respective phase fractions of the gas phase and liquid phase to calculate the respective volume flowrates thereof. However, at the throat of the oil nozzle, the fluid flows in a sonic speed, and the principles of the Venturi pressure difference method are not applicable for metering the fluid flows in a sonic speed.

In current oil fields, nozzles have already been at wellheads, and through the wellheads, subterranean crude oil is ejected. Through long-term production practices, it has been recognized that there are some formulae for showing the quantitative and empirical relations of flowrate of crude oil at these nozzles with the pressure difference $\Delta P$ between the pressure $P_1$ (in oil fields, called as "oil pressure") at the nozzle inlet and the pressure $P_2$ (in oil fields, called as "back pressure") at the nozzle outlet, and the formulae can be useful for approximately estimating the crude oil flowrate. However, such a metering method will involve significant errors. Further, another method that is an actual measuring method during well testing, in which upon testing wells, by measuring pressure and temperature and after separating oil well products, a gas phase and a liquid phase are respectively metered, and then the resultant data is fitted. Such a method is not applicable for long-term applications, because the pressure of the oil wells and the gas mass fraction of the gas phase in the crude oil dynamically vary in a life cycle, and if only a changeless metering equation is used, it will result in significant errors, even misjudge the throughput of the oil wells.

Additionally, it is found that on the precondition that the oil pressure $P_1$ is essentially changeless, when the pressure difference $\Delta P$ gradually rises, the total flowrate $Q$ will also gradually rise; however, when the pressure difference $\Delta P$ reaches and exceeds a certain critical value $\Delta P_c$, the flowrate $Q$ will not change with the change of the $\Delta P$, but be maintained at a stable value without any further changes. Such a state is called as the critical flow state.

Hence, people utilize an oil nozzle to control the throughput of oil wells and the wellhead pressure with the desire the oil nozzle is also able to meter products. However, current oil nozzles have very limited metering functions, and thus they cannot achieve the precise and real-time metering of the respective mass flowrates of the gas phase and liquid phase in a multiphase fluid.

SUMMARY

A first aspect of the invention is provided with a critical flow nozzle flowmeter for measuring respective flowrates of gas phase and liquid phase in a multiphase fluid, comprising the following structural members:
  a throttling nozzle (1) having an inlet, an outlet and a throat, wherein a flow area for the fluid is smallest at the throat;
  a gamma ray detector, comprising a gamma ray emitter (3) and a gamma ray receiver (5), arranged in a way that allows the gamma ray emitted by the gamma ray emitter passing through the cross-section at the inlet of the throttling nozzle in the diametrical direction to reach the gamma ray receiver;
  pressure sensors, respectively for measuring a pressure $P_1$ at the inlet of the throttling nozzle and a pressure $P_2$ at the outlet of the throttling nozzle; and
  a temperature sensor, for measuring a temperature $T_1$ at the inlet of the throttling nozzle.

Preferably, the cross-section area of the throat of the throttling nozzle is $\frac{1}{10}$ to $\frac{1}{2}$ of the cross-section area of the inlet of the throttling nozzle.

Therein, the gamma ray detector is a single-energy gamma ray detector.

A second aspect of the invention relates to a method for measuring the respective flowrates of gas phase and liquid phase in a multiphase fluid, this method uses the critical flow nozzle flowmeter according to the first aspect of the invention and comprises the following steps:

a) measuring a pressure $P_1$ at the inlet and a pressure $P_2$ at the outlet of the throttling nozzle by using the pressure sensors, and measuring a temperature $T_1$ at the inlet of the throttling nozzle by using the temperature sensor;

b) flowing the multiphase fluid through the critical flow nozzle flowmeter in a critical flow manner, wherein the multiphase fluid is judged to reach the critical flow state according to the following method: the symbol "r" is set as a ratio of the pressure at the nozzle outlet to the pressure at the nozzle outlet, $$r = \frac{p_2}{p_1};$$

by measuring the pressure $P_1$ and temperature $T_1$, a density $\rho_{g1}$ of the gas phase is determined; by measuring a mixed density $\rho_m$ with a single-energy gamma ray detector, a gas mass fraction GMF can be determined according to the equation:

$$GMF = \frac{\rho_l - \rho_m}{\rho_l - \rho_{g1}},$$

further to define $$a = \frac{1 - GMF}{GMF} \frac{\rho_{g1}}{\rho_l};$$

according to the characteristic that the gas phase flows in a sonic speed when the multiphase fluid reaches a critical flow state, a critical pressure ratio $r_c$ can be defined by the equation $$r_c = \left[ \frac{a(1 - r_c) + \frac{k}{k-1}}{\frac{k}{k-1} + \frac{k}{2}(1+\alpha)^2} \right]^{\frac{k}{k-1}},$$

and with the equation, the critical pressure $r_c$ can be determined by iterative solution; when a measured pressure ratio r meets $$r = \frac{p_2}{p_1} \leq r_c,$$

the multiphase fluid is judged as a critical flow; in case of a critical flow, by the equation $$s = \sqrt{1 + \frac{\rho_l - \rho_m}{\rho_l - \rho_{g1}} \left( \frac{\rho_l}{\rho_{g1}} - 1 \right)} (1 + 0.6 e^{-5GMF}),$$

a velocity slip ratio between the gas phase and the liquid phase can be calculated; usually, pressure at upstream wellheads is very high, greater than 2 MPa, even up to tens of MPa, while pressure at downstream product lines is generally lower than 1 MPa (usually 500 kPa to 1 Mpa), and thus the pressure ratio $$r = \frac{p_2}{p_1}$$

is very small; hence, once the critical flow nozzle of the invention is mounted and a valve is opened, the multiphase fluid is just in a critical flow state immediately; all the same, it is still necessary to use the above judging method before the formal measurement to assure that the precondition on which the flow calculation is applicable can be satisfied; if the flowing state of the multiphase fluid is verified not to be in a critical flow state, the devices and equations of the invention are not suggested to be used for measurements, and at this time, other methods are used to meter it;

c) respectively calculating a total mass flowrate $Q_m$ of the multiphase fluid, a gas phase mass flowrate $Q_{m,g}$ and a liquid phase mass flowrate $Q_{m,l}$ according to the following equations:

total mass flowrate:

$$Q_m = \sqrt{\frac{CA^2 \rho_{g1} \left[ \alpha(1-r) + \frac{k}{k-1}\left(1 - r^{\frac{k-1}{k}}\right) \right]}{GMF\left(r^{-\frac{1}{k}} + \alpha\right)\left[GMF + \frac{1}{s}(1 - GMF)\right]}}$$

gas phase mass flowrate: $Q_{m,g} = Q_m GMF$
liquid phase mass flowrate: $Q_{m,l} = Q_m (1-GMF)$
wherein:
$Q_m$ is a total mass flowrate, kg/s
$\rho_{g1}$ is a density of the gas phase at the inlet of the throttling nozzle, kg/m$^3$
$\rho_l$ is a density of the liquid phase, kg/m$^3$
GMF is a gas mass fraction
A is a cross-section area of the throat of the throttling nozzle, m$^2$
C is a flow coefficient of the throttling nozzle, being a constant
k is an adiabatic index of gas
r is a ratio of the pressure at the nozzle outlet to the pressure at the nozzle inlet, $$r = \frac{p_2}{p_1}$$

s is a velocity slip ratio between the gas phase and the liquid phase, $$s = \frac{u_g}{u_l}.$$

The invention has the following advantages:

1. The invention creatively uses a single-energy gamma ray detector in the combination of a critical flow nozzle to measure the respective mass flowrates of the gas phase and liquid phase in a multiphase fluid, wherein the single-energy gamma ray detector can measure the gas-liquid mixed density in real time. In the prior art, critical flow nozzle meters are also present, whereas these meters are only used for approximate estimation of the total flow of a gas-liquid mixture, but cannot achieve the real-time and precise measurements of the respective mass flowrates of gas phase and liquid phase in a multiphase fluid.

2. The invention, directed to the above original metering device, specially uses some original equations to calculate the mass flowrates of the gas phase and liquid phase in a critical flow state.

Figure 1:
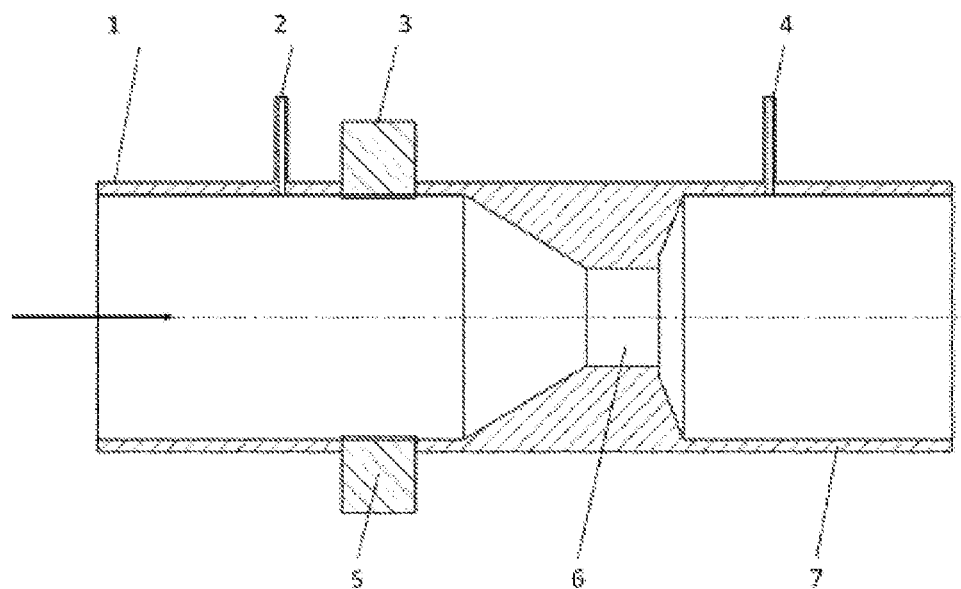
FIG. 1 is a schematic diagram of the critical flow nozzle flowmeter according to the invention.
Figure 2:
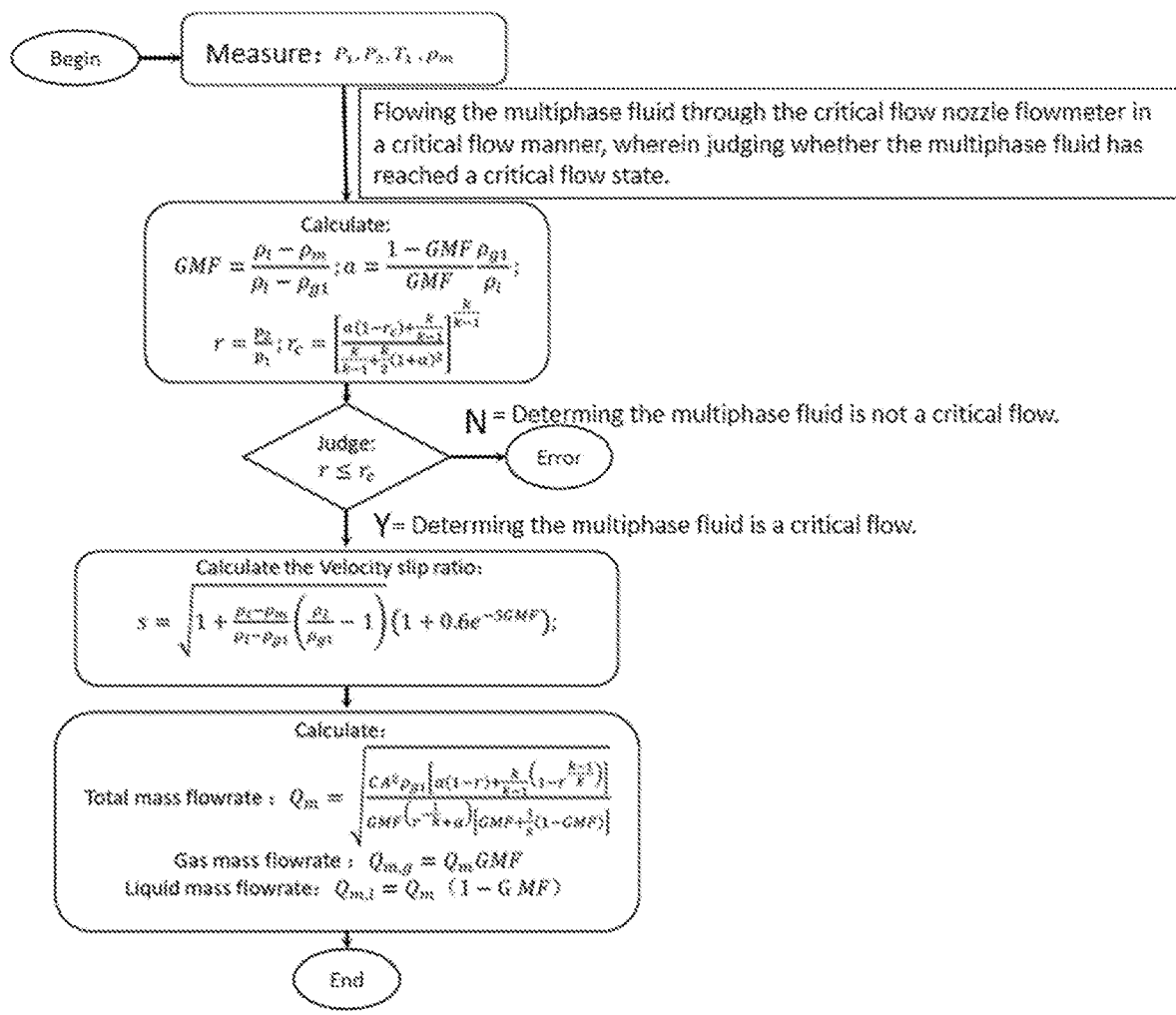
FIG. 2 is a flow chart of the method for measuring respective flowrates of a gas phase and a liquid phase in a multiphase fluid using the critical flow nozzle flowmeter.

In the above FIGURE, the reference symbols have the following meanings:

1. Oil nozzle connection port; 2. Pressure and temperature composite sensor; 3. Gamma ray emitter; 4. Pressure sensor; 5. Gamma ray receiver; 6. Oil nozzle throat; 7. Oil nozzle outlet.

The above FIGURE is only used for exemplarily describing the invention, but not restricting the invention in any manner.

DETAILED DESCRIPTION OF THE EMBODIMENTS

As below described, there is a method of measuring the respectively flowrates of the gas phase and liquid phase in a multiphase fluid using the critical flow nozzle flowmeter according to the invention, comprising the following steps:

a) measuring a pressure $P_1$ at the inlet and a pressure $P_2$ at the outlet of the throttling nozzle by using pressure sensors, and measuring a temperature $T_1$ at the inlet of the throttling nozzle by using a temperature sensor;

b) flowing the multiphase fluid through the critical flow nozzle flowmeter in a critical flow manner, wherein the multiphase fluid is judged to reach the critical flow state according to the following method: the symbol "r" is set as a ratio of the pressure at the nozzle outlet to the pressure at the nozzle outlet, $$r = \frac{p_2}{p_1};$$

by measuring the pressure $P_1$ and temperature $T_1$, a density $\rho_{g1}$ of the gas phase is determined; by measuring a mixed density $\rho_m$ with a single-energy gamma ray detector, a gas mass fraction GMF can be determined according to the equation:

$$GMF = \frac{\rho_l - \rho_m}{\rho_l - \rho_{g1}},$$

further to define $$a = \frac{1 - GMF}{GMF} \frac{\rho_{g1}}{\rho_l};$$

according to the characteristic that the gas phase flows in a sonic speed when the multiphase fluid reaches a critical flow state, a critical pressure ratio $r_c$ can be defined by the equation $$r_c = \left[ \frac{a(1 - r_c) + \frac{k}{k-1}}{\frac{k}{k-1} + \frac{k}{2}(1 + \alpha)^2} \right]^{\frac{k}{k-1}},$$

and with the equation, the critical pressure $r_c$ can be determined by iterative solution; when a measured pressure ratio r meets $$r = \frac{p_2}{p_1} \leq r_c,$$

the multiphase fluid is judged as a critical flow; in case of a critical flow, by the equations $$= \sqrt{1 + \frac{\rho_l - \rho_m}{\rho_l - \rho_{g1}} \left( \frac{\rho_l}{\rho_{g1}} - 1 \right)} (1 + 0.6e^{-5GMF}),$$

a velocity slip ratio between the gas phase and the liquid phase can be calculated;

c) respectively calculating a total mass flowrate $Q_m$ of the multiphase fluid, a gas phase mass flowrate $Q_{m,g}$ and a liquid phase mass flowrate $Q_{m,l}$ according to the following equations:

total mass flowrate:

$$Q_m = \sqrt{\frac{CA^2 \rho_{g1} \left[ \alpha(1 - r) + \frac{k}{k-1} \left( 1 - r^{\frac{k-1}{k}} \right) \right]}{GMF\left( r^{-\frac{1}{k}} + \alpha \right) \left[ GMF + \frac{1}{s}(1 - GMF) \right]}}$$

gas phase mass flowrate: $Q_{m,g} = Q_m GMF$ liquid phase mass flowrate: $Q_{m,l} = Q_m (1 - GMF)$ wherein:

$Q_m$ is a total mass flowrate, kg/s $\rho_{g1}$ is a density of the gas phase at the inlet of the throttling nozzle, kg/m³

$\rho_l$ is a density of the liquid phase, kg/m³

GMF is a gas mass fraction

A is a cross-section area of the throat of the throttling nozzle, m²

C is a flow coefficient of the throttling nozzle, being a constant k is an adiabatic index of gas r is a ratio of the pressure at the nozzle outlet to the pressure at the nozzle inlet, $$r = \frac{p_2}{p_1}$$

s is a velocity slip ratio between the gas phase and the liquid phase, $$s = \frac{u_g}{u_l}.$$

The invention claimed is:

1. A method for measuring respective flowrates of a gas phase and a liquid phase in a multiphase fluid using a critical flow nozzle flowmeter, wherein the critical flow nozzle flowmeter comprises:
   a throttling nozzle having an inlet, an outlet and a throat; wherein the throat has a smallest flow area for flowing fluid compared with the inlet and the outlet; and a cross-section area of the throat of the throttling nozzle is 1/10 to 1/2 of a cross-section area of the inlet of the throttling nozzle;
   a gamma ray detector comprising a gamma ray emitter and a gamma ray receiver, and the gamma ray detector is arranged in a way allowing a gamma ray emitted by the gamma ray emitter to pass through a cross-section at the inlet of the throttling nozzle in a diametrical direction to reach at the gamma ray receiver; and the gamma ray detector is a single-energy gamma ray detector;
   pressure sensors respectively configured for measuring a pressure $P_1$ at the inlet of the throttling nozzle and a pressure $P_2$ at the outlet of the throttling nozzle; and
   a temperature sensor configured for measuring a temperature $T_1$ at the inlet of the throttling nozzle;
   and the method comprises the following steps:
   a) measuring the pressure $P_1$ at the inlet and the pressure $P_2$ at the outlet of the throttling nozzle by using the pressure sensors, and measuring the temperature $T_1$ at the inlet of the throttling nozzle by using the temperature sensor;
   b) flowing the multiphase fluid through the critical flow nozzle flowmeter in a critical flow manner, wherein judging whether the multiphase fluid has reached a critical flow state according to the following method:
   setting a symbol "r" as a ratio of the pressure $P_2$ at the outlet to the pressure $P_1$ at the inlet, and $$r = \frac{p_2}{p_1};$$

measuring the pressure $P_1$ and the temperature $T_1$ to determine a density $\rho_{g1}$ of the gas phase; measuring a mixed density $\rho_m$ with the single-energy gamma ray detector to determine a gas mass fraction GMF according to a first equation:

$$GMF = \frac{\rho_l - \rho_m}{\rho_l - \rho_{g1}},$$

and further defining $$a = \frac{1 - GMF}{GMF} \frac{\rho_{g1}}{\rho_l};$$

according to a characteristic, i.e., the gas phase flows in a sonic speed when the multiphase fluid reaches the critical flow state, defining a critical pressure ratio $r_c$ by a second equation $$r_c = \left[ \frac{a(1 - r_c) + \frac{k}{k-1}}{\frac{k}{k-1} + \frac{k}{2}(1+\alpha)^2} \right]^{\frac{k}{k-1}},$$

and with the second equation, determining the critical pressure $r_c$ by iterative solution; when a measured pressure ratio r meets $$r = \frac{p_2}{p_1} \leq r_c,$$

determining the multiphase fluid is a critical flow; in case of a critical flow, through a third equation $$s = \sqrt{1 + \frac{\rho_l - \rho_m}{\rho_l - \rho_{g1}} \left( \frac{\rho_l}{\rho_{g1}} - 1 \right)} (1 + 0.6e^{-5GMF}),$$

calculating a velocity slip ratio between the gas phase and the liquid phase; and
   c) respectively calculating a total mass flowrate $Q_m$ of the multiphase fluid, a gas phase mass flowrate $Q_{m,g}$ and a liquid phase mass flowrate $Q_{m,l}$ according to the following equations:
   the total mass flowrate:

$$Q_m = \sqrt{\frac{CA^2 \rho_{g1} \left[ \alpha(1-r) + \frac{k}{k-1}\left(1 - r^{\frac{k-1}{k}}\right) \right]}{GMF\left(r^{-\frac{1}{k}} + \alpha\right)\left[GMF + \frac{1}{s}(1 - GMF)\right]}};$$

the gas phase mass flowrate: $Q_{m,g} = Q_m GMF$; and
the liquid phase mass flowrate: $Q_{m,l} = Q_m(1-GMF)$;
wherein:
$Q_m$ is the total mass flowrate, kg/s;
$\rho_{g1}$ is a density of the gas phase at the inlet of the throttling nozzle, kg/m$^3$;
$\rho_l$ is a density of the liquid phase, kg/m$^3$;
GMF is a gas mass fraction;
A is the cross-section area of the throat of the throttling nozzle, m$^2$;
C is a flow coefficient of the throttling nozzle and is a constant;
k is an adiabatic index of gas;
r is a ratio of the pressure $P_2$ at the nozzle outlet to the pressure $P_1$ at the inlet, and $$r = \frac{p_2}{p_1};$$

and
s is a velocity slip ratio between the gas phase and the liquid phase.

* * * * *